US010213615B2

(12) United States Patent
Gale et al.

(10) Patent No.: US 10,213,615 B2
(45) Date of Patent: Feb. 26, 2019

(54) SYSTEM AND METHOD FOR MICROMAGNETIC STIMULATION OF THE CENTRAL NERVOUS SYSTEM

(71) Applicant: THE CLEVELAND CLINIC FOUNDATION, Cleveland, OH (US)

(72) Inventors: John T. Gale, Cleveland, OH (US); Hyun-Joo Park, Cleveland, OH (US); Matthew Johnson, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 719 days.

(21) Appl. No.: 14/203,921

(22) Filed: Mar. 11, 2014

(65) Prior Publication Data
US 2014/0275719 A1 Sep. 18, 2014

Related U.S. Application Data

(60) Provisional application No. 61/793,537, filed on Mar. 15, 2013.

(51) Int. Cl.
A61N 2/00 (2006.01)
A61N 2/02 (2006.01)

(52) U.S. Cl.
CPC ............... *A61N 2/006* (2013.01); *A61N 2/02* (2013.01)

(58) Field of Classification Search
CPC ........... A61N 2/00; A61N 2/004; A61N 2/008
USPC ......................................................... 600/14
See application file for complete search history.

(56) References Cited

U.S. PATENT DOCUMENTS

| 711,431 | A | 10/1902 | Lorenz et al. |
| 5,066,272 | A | 11/1991 | Eaton et al. |
| 7,305,268 | B2 | 12/2007 | Gliner et al. |
| 7,395,268 | B2 | 7/2008 | Kobayashi |
| 8,195,300 | B2 | 6/2012 | Gliner et al. |
| 8,301,226 | B2 | 10/2012 | Csavoy et al. |
| 9,095,266 | B1* | 8/2015 | Fu ..................... A61B 5/0476 |
| 2005/0159792 | A1* | 7/2005 | Ridder ..................... A61N 1/00 607/57 |
| 2005/0228209 | A1* | 10/2005 | Schneider .......... A61B 5/04009 600/13 |

(Continued)

FOREIGN PATENT DOCUMENTS

EP 0709115 A1 5/1996

OTHER PUBLICATIONS

Erez et al., "Generalized framework for stimulus artifact removal." Journal of neuroscience methods 191.1 (2010): 45-59.

(Continued)

*Primary Examiner* — Charles A Marmor, II
*Assistant Examiner* — Joshua D Lannu
(74) *Attorney, Agent, or Firm* — Tarolli, Sundheim, Covell & Tummino LLP

(57) ABSTRACT

One aspect of the present disclosure relates a system that can employ micromagnetic stimulation to activate or suppress one or more areas of the central nervous system. A portion of the central nervous system can be exposed. A probe can be configured to be located in proximity to the exposed portion of the nervous system. A microcoil (of a size less than or equal to 10 millimeters) can be coupled to the probe and configured to activate or suppress the portion of the central nervous system via electromagnetic induction.

11 Claims, 12 Drawing Sheets

(56) References Cited

U.S. PATENT DOCUMENTS

| | | | |
|---|---|---|---|
| 2006/0095088 A1* | 5/2006 | De Ridder | A61N 1/3605 607/48 |
| 2007/0027514 A1* | 2/2007 | Gerber | A61N 1/05 607/116 |
| 2008/0045775 A1* | 2/2008 | Lozano | A61N 1/36014 600/12 |
| 2009/0254146 A1 | 10/2009 | Bonmassar et al. | |
| 2010/0130945 A1 | 5/2010 | Laniado et al. | |
| 2011/0301665 A1 | 12/2011 | Mercanzini et al. | |
| 2013/0178693 A1* | 7/2013 | Neuvonen | A61B 5/0042 600/13 |

OTHER PUBLICATIONS

Fabre, Jennifer M., et al. "Falls risk factors and a compendium of falls risk screening instruments." Journal of geriatric physical therapy 33.4 (2010): 184-197.

Finlayson et al., "Alterations in the spontaneous discharge patterns of single units in the dorsal cochlear nucleus following intense sound exposure." Hearing research 256.1 (2009): 104-117.

Fregni et al., "Technology insight: noninvasive brain stimulation in neurology—perspectives on the therapeutic potential of rTMS and tDCS." Nature Clinical Practice Neurology 3.7 (2007): 383-393.

Greenberg, B. D., et al. "Deep brain stimulation of the ventral internal capsule/ventral striatum for obsessive-compulsive disorder: worldwide experience." Molecular psychiatry 15.1 (2010): 64-79.

Guskiewicz "Postural stability assessment following concussion: one piece of the puzzle." Clinical Journal of Sport Medicine 11.3 (2001): 182-189.

Heath "Electrical self-stimulation of the brain in man." American Journal of Psychiatry 120.6 (1963): 571-577.

Henderson et al. "Permanent neurological deficit related to magnetic resonance imaging in a patient with implanted deep brain stimulation electrodes for Parkinson's disease: case report." Neurosurgery 57.5 (2005): E1063.

Hunt et al. "Concussion assessment and management." Clinics in sports medicine 29.1 (2010): 5-17.

Lee et al. "Synthesis and application of virus-based hybrid nanomaterials." Biotechnology and bioengineering 109.1 (2012): 16-30.

Loddenkemper, et al. "Deep brain stimulation in epilepsy." Journal of Clinical Neurophysiology 18.6 (2001): 514-532.

Machado et al. "Chronic electrical stimulation of the contralesional lateral cerebellar nucleus enhances recovery of motor function after cerebral ischemia in rats." Brain research 1280 (2009): 107-116.

Machado et al. "Deep brain stimulation for movement disorders: patient selection and technical options." Cleveland Clinic journal of medicine 79.Suppl 2 (2012): S19-S24.

Machado et al. "Deep brain stimulation: What can patients expect from it?." Cleveland Clinic journal of medicine 79.2 (2012): 113-120.

Machado et al. "Upside down crossed cerebellar diaschisis: proposing chronic stimulation of the dentatothalamocortiacal pathway for post-stroke motor recovery." Frontiers in integrative neuroscience 6 (2012).

Machado, Andre G., et al. "Cerebral stimulation for the affective component of neuropathic pain." Neuromodulation: Technology at the Neural Interface 16.6 (2013): 514-518.

Malone, et al. "Deep brain stimulation of the ventral capsule/ventral striatum for treatment-resistant depression." Biological psychiatry 65.4 (2009): 267-275.

Manzoor et al. "Noise-induced hyperactivity in the inferior colliculus: its relationship with hyperactivity in the dorsal cochlear nucleus." Journal of neurophysiology 108.4 (2012): 976-988.

Mauger et al. "An in vivo investigation of first spike latencies in the inferior colliculus in response to multichannel penetrating auditory brainstem implant stimulation." Journal of neural engineering 7.3 (2010): 036004.

McCaffrey et al. "Measurement of Head Impacts in Collegiate Football Players: Clinical Measures of Concussion After High-and Low-Magnitude Impacts." Neurosurgery 61.6 (2007): 1236-1243.

Merrill et al. "Electrical stimulation of excitable tissue: design of efficacious and safe protocols." Journal of neuroscience methods 141.2 (2005): 171-198.

Montgomery et al. "Mechanisms of action of deep brain stimulation (DBS)." Neuroscience & Biobehavioral Reviews 32.3 (2008): 388-407.

Montgomery "The epistemology of deep brain stimulation and neuronal pathophysiology." Frontiers in integrative neuroscience 6 (2012).

Muggleton et al. "Smaller magnets for smarter minds?." Trends in cognitive sciences 16.9 (2012): 452-453.

Oliveira et al., "Calculation of area of stabilometric signals using principal component analysis." Physiological measurement 17.4 (1996): 305.

Pascual-Leone et al., "Transcranial magnetic stimulation in cognitive neuroscience—virtual lesion, chronometry, and functional connectivity." Current opinion in neurobiology 10.2 (2000): 232-237.

Peterchev et al., "Repetitive transcranial magnetic stimulator with controllable pulse parameters." Journal of neural engineering 8.3 (2011): 036016.

Plow et al., "Brain stimulation in the treatment of chronic neuropathic and non-cancerous pain." The Journal of Pain 13.5 (2012): 411-424.

Plow et al. "Invasive Cortical Stimulation to Promote Recovery of Function After Stroke a Critical Appraisal." Stroke 40.5 (2009): 1926-1931.

Pollak et al. "Effets de la stimulation du noyau sous-thalamique dans la maladie de Parkinson." Revue neurologique 149.3 (1993): 175-176. English Translation of Abstract Attached.

Ruohonen et al., "Coil optimization for magnetic brain stimulation." Annals of biomedical engineering 25.5 (1997): 840-849.

Shum et al. "Children with attention deficit hyperactivity disorder have impaired balance function: involvement of somatosensory, visual, and vestibular systems." The Journal of pediatrics 155.2 (2009): 245-249.

The Lancet "Surgery for Parkinson's Disease", Neurology, vol. 3, Dec. 2004, pp. 726-728.

Spiegel et al. "Transient dystonia following magnetic resonance imagingin a patient with deep brain stimulation electrodes for the treatment of Parkinson disease: Case report." Journal of neurosurgery 99.4 (2003): 772-774.

Walter et al., "Surgical treatment for Parkinson's disease." The Lancet Neurology 3.12 (2004): 719-728.

Vitek et al. "Intraoperative neurophysiology in DBS for dystonia." Movement Disorders 26.S1 (2011): S31-S36.

Whitney et al. "A comparison of accelerometry and center of pressure measures during computerized dynamic posturography: a measure of balance." Gait & posture 33.4 (2011): 594-599.

Winter "Human balance and posture control during standing and walking." Gait & posture 3.4 (1995): 193-214.

Winter et al. "Unified theory regarding A/P and M/L balance in quiet stance." Journal of neurophysiology 75.6 (1996): 2334-2343.

Adlerton et al. "Forceplate and accelerometer measures for evaluating the effect of muscle fatigue on postural control during one-legged stance." Physiotherapy Research International 8.4 (2003): 187-199.

Barker et al. "Non-invasive magnetic stimulation of human motor cortex." The Lancet 325.8437 (1985): 1106-1107.

Barros et al., "Effects of electrotactile vestibular substitution on rehabilitation of patients with bilateral vestibular loss." Neuroscience letters 476.3 (2010): 123-126.

Bonmassar et al. "Microscopic magnetic stimulation of neural tissue." Nature communications 3 (2012): 921.

International Search Report for PCT/US2014/023083, dated Jun. 24, 2014, pp. 1-12.

* cited by examiner

SYSTEM AND METHOD FOR MICROMAGNETIC STIMULATION OF THE CENTRAL NERVOUS SYSTEM

RELATED APPLICATIONS

This application claims the benefit of U.S. Provisional Application No. 61/793,537, filed Mar. 15, 2013, entitled "Acute Intra-Cranial Micromagnetic Stimulation," the entirety of which is hereby incorporated by reference for all purposes.

TECHNICAL FIELD

The present disclosure relates generally to micromagnetic stimulation of the central nervous system and, more specifically, to systems and methods that can employ micromagnetic stimulation to activate one or more areas of the central nervous system.

BACKGROUND

A number of neurosurgical procedures, including epilepsy resections, tumor resections and chronic neuroprosthetic implantations, require functional mapping of the conduction within central nervous system. A site in the central nervous system can be stimulated and the subsequent activation from the stimulation can be mapped to understand the conduction in the brain. Generally, such functional mapping requires multiple sites within the central nervous system to be stimulated via electrical stimulation and/or magnetic stimulation.

An electrical stimulation current can be applied to the exposed central nervous system tissue via at least one of the metal contact. The current spreads between the contacts and activates at least part of the exposed central nervous system tissue. A primary limitation of the electrical stimulation probe is due to the contacts being located on the surface of the exposed central nervous system tissue. Accordingly, a predominate amount of current flows between the contacts, and a smaller amount of current flows into the exposed central nervous system tissue. One alternative that can increase the amount of current that flows into the tissue is increasing the amplitude of the current. However, increasing the amplitude of the current reduces the spatial resolution if the electrical stimulation by activating untargeted neurons. Another alternative that can increase the amount of current that flows into the tissue is inserting the probe into the tissue (referred to as penetration mapping). While inserting the probe into the tissue would increase spatial resolution and decrease the stimulation amplitude needed to activate the tissue, penetration mapping techniques are not typically used at least because inserting the probe into the tissue may lead to surgical complications and damage of tissue that is otherwise normal.

Traditional magnetic stimulation techniques use magnetic induction to activate at least part of the central nervous system. While these magnetic stimulation techniques do not require the central nervous system to be exposed, they suffer from a lack of specificity so that the activation cannot be mapped accurately. Additionally, traditional magnetic stimulation techniques employ a large inductor coil (e.g., many centimeters in size) that requires a large power source, adding additional instrumentation to the surgical area and generates a large current that can induce heating in metal objects, such as surgical instruments.

SUMMARY

The present disclosure relates generally to micromagnetic stimulation of the central nervous system and, more specifically, to systems and methods that can employ micromagnetic stimulation to activate one or more areas of the central nervous system. Micromagnetic stimulation overcomes the obstacles of both traditional electrical stimulation and traditional magnetic stimulation.

In one aspect, the present disclosure can include a system that employs micromagnetic stimulation to activate a portion of the central nervous system. The system can include a probe configured to be located in proximity to an exposed portion of the central nervous system. The system can also include a microcoil (of a size less than or equal to 10 millimeters) coupled to the probe and configured to activate the portion of the central nervous system via electromagnetic induction.

In another aspect, the present disclosure can include a method for mapping activation in a central nervous system of a subject. The method can include one or more steps that can include: exposing at least a portion of the central nervous system; placing a probe, coupled to a microcoil of a size less than or equal to 10 millimeters, in proximity to a portion of tissue within the exposed at least a portion of the central nervous system; producing, by the microcoil, a time-varying magnetic field and inducing a current flow to activate the portion of tissue; and mapping the activation of the portion of tissue. The mapping step can be performed by a system that includes a processor.

In a further aspect, the present disclosure can include a method for electrically stimulating a portion of the central nervous system of a subject. The method can include steps that can include: exposing at least a portion of the central nervous system; placing a probe, coupled to a microcoil of a size less than or equal to 10 millimeters, in proximity to a portion of tissue within the exposed at least a portion of the central nervous system; and producing, by the microcoil, a time-varying magnetic field and inducing a current flow to stimulate the portion of tissue.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
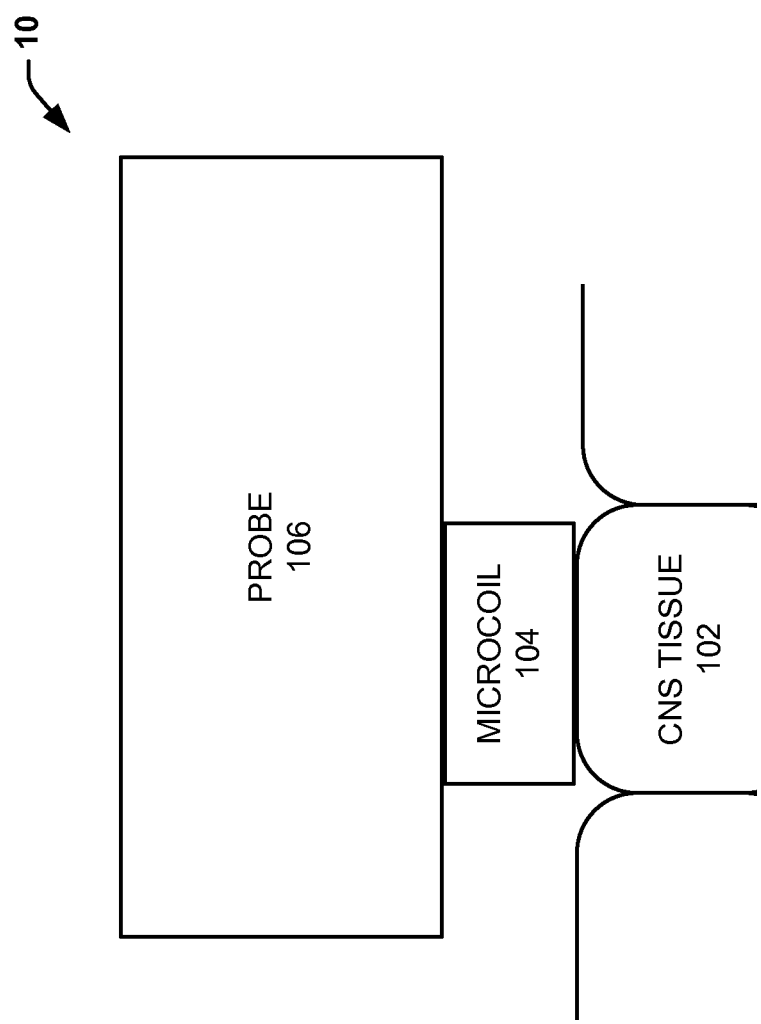
FIG. 1 is a schematic block diagram showing a system that employs micromagnetic stimulation to activate one or more areas of the central nervous system in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "central nervous system" can refer to a patient's brain and/or spinal cord. At least a portion of the central nervous system can be exposed during a neurosurgical procedure.

As used herein, the term "exposed" can refer to a portion of the central nervous system that is made accessible for an external device (e.g., one or more microcoils) to be placed in proximity to or in contact with the portion of the central nervous system. The portion of the central nervous system can be exposed during a neurosurgical procedure.

As used herein, the term "neurosurgical procedure" can refer to a surgical procedure that relates to at least a portion of a patient's central nervous system. At least a portion of the neurosurgical procedure can be conducted based on a functional map created by neural stimulation of the portion of the central nervous system. Examples of neurosurgical procedures can include epilepsy resections, tumor resections, and chronic neuroprosthetic implantations (e.g., for deep brain stimulation, spinal cord stimulation, etc.).

As used herein, the term "neural stimulation" can refer to the activation of one or more nerves through an external source. For example, the external source can cause a nerve to generate an action potential.

As used herein, the term "activation" or "activate" can refer causing a nerve to conduct. For example, the conduction can include the generation of an action potential in an axon of the nerve and/or the release of neurotransmitter from the terminal of a nerve. An activated nerve can, in turn, activate one or more other nerves, causing these activated nerves to conduct. As an example, activation of a portion of the central nervous system can include the activation of one or more nerves within a portion of the brain in proximity to a magnetic stimulation and the subsequent activation of additional nerves in a different area of the brain.

As used herein, the term "magnetic stimulation" can refer to a type of neural stimulation provided by an external device that employs electromagnetic induction to activate one or more nerves.

As used herein, the term "micromagnetic stimulation" can refer to an acute magnetic stimulation that can target a small number of nerves (e.g., for functional mapping of the central nervous system) by utilizing inductors (e.g., microcoils) that provide the electromagnetic induction to stimulate the small number of nerves.

As used herein, the term "microcoil" or "microcoil inductor" can refer to an inductor (e.g., of a size less than or equal to 10 millimeters) of a geometry (e.g., a coiled geometry) utilized in micromagnetic stimulation. The microcoil can focus the magnetic fields into the central nervous system tissue and allow the generation of an electrical gradient at a depth within the tissue.

As used herein, the term "functional mapping" can relate to the co-localization of conduction within the central nervous system with anatomical features of the central nervous system. In one example, the conduction can be mapped by an application of neural stimulation to at least a part of an exposed portion of the central nervous system (e.g., targeted to an area of the central nervous system via micromagnetic stimulation). Functional mapping can also be referred to herein as "activation mapping" and/or "mapping."

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "subject" and "patient" can be used interchangeably herein.

As used herein, the term "medical professional" can refer to any person involved the conducting a neurosurgical procedure including, but not limited to, physicians, medical students, nurse practitioners, nurses, and other operating room staff.

II. Overview

The present disclosure relates generally to micromagnetic stimulation of the central nervous system and, more specifically, to systems and methods that can employ micromagnetic stimulation to activate one or more areas of the central nervous system during a neurosurgical procedure. The activation (e.g., based on the micromagnetic stimulation and subsequent conduction) can be mapped in a functional map that is used in a neurosurgical procedure. In some instances, the systems and methods described herein can employ microcoils (e.g., of a size less than 10 millimeters) to accomplish the micromagnetic stimulation. Micromagnetic stimulation is advantageous over both traditional electrical stimulation and traditional magnetic stimulation.

Traditional magnetic stimulation is advantageous over traditional electrical stimulation, which injects charge into the surrounding tissue between contacts. In magnetic stimulation, current is induced in central nervous system tissue by time varying magnetic fields emanating from an inductor without injecting charge into the tissue. The current in the tissue can be generated due to ion displacement in the tissue with no net charge injected to the tissue, mitigating the deleterious oxidation or reduction phenomenon and the electrode-tissue interface due to injected charge. However, the spatial resolution of traditional magnetic stimulation is poor and requires a large amount of current that can lead to heating and interference.

Micromagnetic stimulation is advantageous over traditional magnetic stimulation. Micromagnetic stimulation utilizes smaller magnetic coils that have a better spatial resolution than traditional magnetic stimulation and requires a smaller amount of current that does not lead to the same heating and interference of traditional magnetic stimulation. In micromagnetic stimulation, microcoil inductors ("microcoils") can be designed with a geometry selected to focus stimulation and located in proximity to or in contact with the surface of exposed central nervous system tissue to focus the magnetic fields into the tissue. Stimulation through the microcoils can allow for the generation of an electrical gradient at a depth within the tissue to activate one or more nerves in the tissue. A current can be generated in the nerve based on the electrical gradient (e.g., an action potential can be transmitted by an axon of the nerve if the electrical gradient is above a threshold voltage for conduction).

III. Systems

One aspect of the present disclosure can include systems that can activate one or more areas of the central nervous system with micromagnetic stimulation. Although not wishing to be bound by theory, it is believed that microcoils used in micromagnetic stimulation can focus a magnetic field at a depth into a tissue (based on the geometry and/or size of the microcoils), allowing for the targeted generation of an electrical gradient at the depth within the tissue to activate one or more nerves (e.g., an action potential can be transmitted by an axon of a nerve if the electrical gradient is above a threshold voltage for conduction and the conduction can be transmitted to another nerve), allowing for mapping of the activation in the central nervous system. An example of a system 10 that can employ micromagnetic stimulation to activate one or more areas of the central nervous system is shown in FIG. 1. Another example of a system 30 that can map activation in a central nervous system of a subject is shown in FIG. 4.

Figure 2:
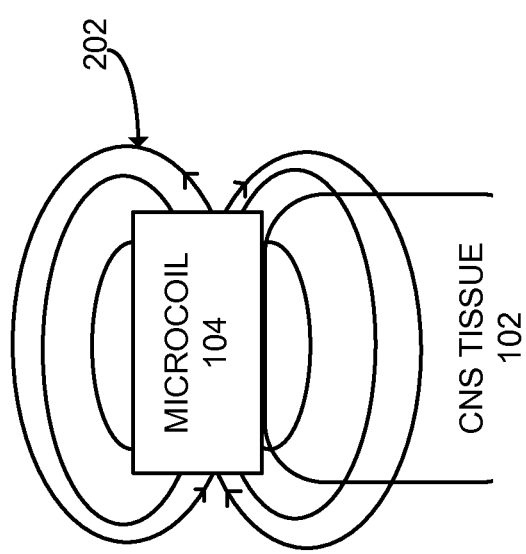
FIG. 2 is a schematic diagram showing the magnetic field produced by the microcoil in the system of FIG. 1.
Figure 3:
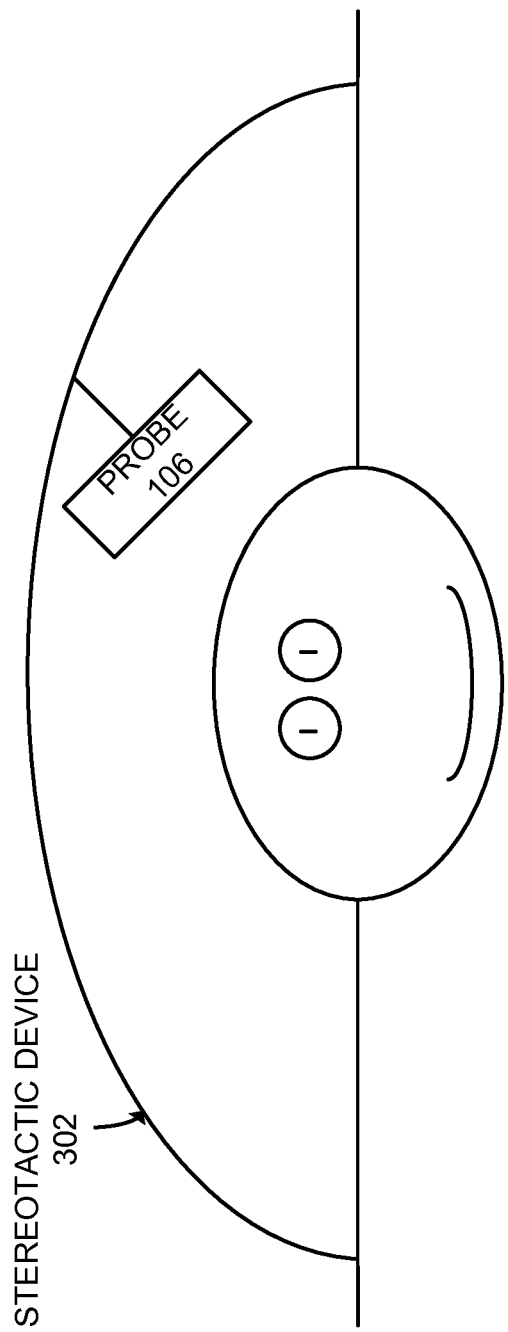
FIG. 3 is a schematic diagram showing the probe in the system of FIG. 1 attached to a stereotactic device.
Figure 4:
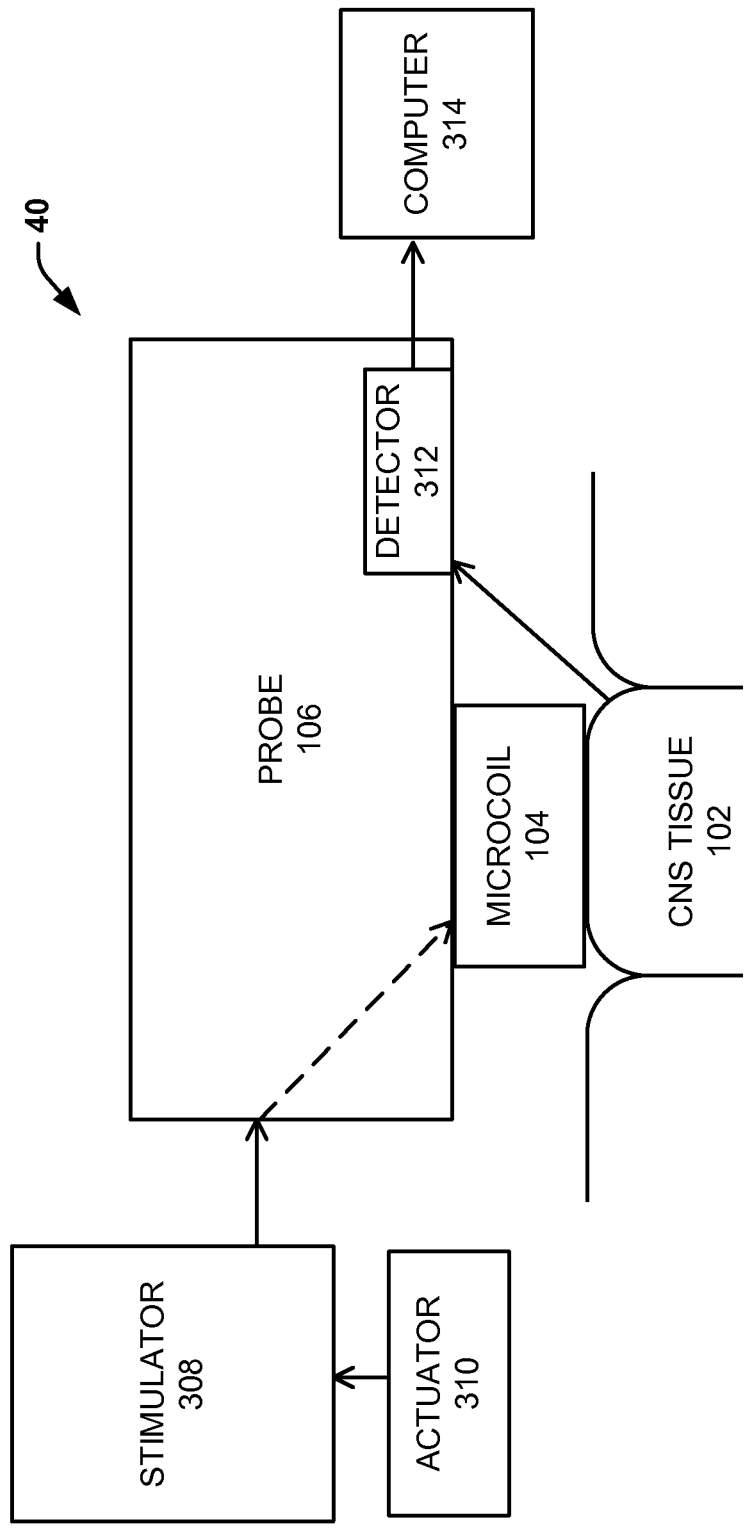
FIG. 4 is a schematic block diagram showing a system that maps activation in a central nervous system of a subject in accordance with another aspect of the present disclosure.

FIG. 1, as well as associated FIGS. 2-3, and FIG. 4 are illustrated schematically as block diagrams of systems with the different blocks representing different components. The functions of one or more of the components (e.g., probe 306, stimulator 308, actuator 310, detector 312 and/or computer 314) can be implemented by computer program instructions. These computer program instructions can be stored in a non-transitory memory and provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the components specified in the block diagrams.

As shown in FIG. 1, one aspect of the present disclosure can include a system 10 configured to employ micromagnetic stimulation to activate one or more areas of the central nervous system. In micromagnetic stimulation, when a time-varying current is applied to a microcoil 104, the microcoil can generate a time-varying magnetic field. Temporal changes in the magnetic field can induce an electrical field in one or more areas of the central nervous system 102. The electrical field can cause one or more axons within the portion of the central nervous system 102 to go over a threshold voltage and produce an action potential and/or cause the release of one or more neurotransmitters from an axon's terminal. Conduction of the action potential and/or release of the neurotransmitters can trigger the activation and/or suppression of one or more additional neurons in the portion of the central nervous system 102 and/or other parts of the central nervous system. The activation and/or suppression of the portion of the central nervous system 102 and any subsequent regions can be mapped to create an activation map that can be used in a neurosurgical procedure.

As described above, the micromagnetic stimulation of system 10 is advantageous over traditional electrical stimulation and magnetic stimulation at least because micromagnetic stimulation can generate at least one of conduction and release of neurotransmitter within the central nervous system with high specificity (e.g., allowing for activation mapping) without injecting charge into the tissue. The micromagnetic stimulation of system 10 can exhibit a higher spatial resolution than traditional magnetic stimulation without causing unfavorable heating (e.g., of metal surgical instruments, metal stereoscopic head frames, and the like), electromagnetic interference (e.g., with electronic equipment, etc.) and/or demagnetization (e.g., of ID badges, credit cards, and the like). The micromagnetic stimulation is also favorable to traditional electrical stimulation because no net charge is delivered to the tissue, causing no damaging reduction and/or oxidation reactions in the tissue. Additionally, the microcoils 104 used in micromagnetic stimulation do not puncture the tissue like the contacts used for some traditional electrical stimulation techniques.

The system 10 can include components that can facilitate the micromagnetic stimulation, including the microcoil 104 (e.g., of a size less than or equal to 10 millimeters) and a probe 16 that is physically coupled and/or electrically coupled to the microcoil. The microcoil 104 and/or the probe 106 can be configured to be located in proximity to or contacting the surface of an exposed portion of the central nervous system 102.

The microcoil 104 can be configured to activate the portion of the central nervous system 102 via electromagnetic induction. A time-varying current can be applied to the microcoil 104 (e.g., by a stimulator device within the probe 106 and/or electrically coupled to the microcoil and/or the probe). In response to the time-varying current, the microcoil can generate a time-varying magnetic field, which can induce an electrical field the portion of the central nervous system. The electrical field can create a voltage drop that causes one or more neurons within the portion of the central nervous system to activate. For example, the electromagnetic induction can activate and/or suppress one or more neurons within the portion of the central nervous system 102 (causing the generation of an action potential in the one or more neurons), and the neurons can conduct to activate and/or suppress a second one or more nerves (not necessarily within the portion of the central nervous system).

As shown in FIG. 2, the microcoil 104 can emanate a time-varying magnetic field 202 in response to a time-varying electric current delivered to the microcoil. The time-varying magnetic field 202 can allow for the generation of an electrical gradient at a depth within the tissue of the portion of the central nervous system 102 to induce an activating current flow within one or more nerves within the portion of the central nervous system 102. The one or more nerves can be a focus of the stimulation based on the geometric shape and/or size of the microcoil 104. For example, the placement of the probe 106, and/or the geometric shape and/or size of the microcoil 104 can be selected based on the intended focus of the stimulation.

In some instances, the size and/or geometric of the microcoil 104 can focus the magnetic fields in different ways (e.g., to activate different portions of the central nervous system). For example, the microcoil 104 can be of a size less than or equal to 10 millimeters. In a further example, the microcoil 104 can be of a size less than or equal to 3 millimeters. In another example, the microcoil 104 can be of a size less than or equal to 1 millimeter. Because the microcoil 104 are of a small size and placed in close proximity to (or on the surface of) the exposed portion of the central nervous system 102, they require magnitudes less energy to generate the time-varying magnetic field 202 capable of activating the central nervous system tissue than traditional magnetic stimulation, so the heating and electromagnetic interference generated by the microcoil can be minimal and difficult to detect in the background environment.

Referring again to FIG. 1, the probe 106 can be coupled to the microcoil 104. The probe 106 can be configured to bring the microcoil 104 into close proximity to or in contact with the exposed portion of the central nervous system 102. The probe 106 can be designed with different configurations to match specific surgical objectives. As an example, the probe 106 can be configured to be held by a medical professional so that the microcoil 104 can be placed in proximity to or in contact with the exposed portion of the central nervous system. In another example, the probe 106 can be attached to a mounting apparatus and/or a surgical instrument to take advantage of current imaging and stereotactic practices.

One example of the probe 106 being attached to a surgical instrument is shown in FIG. 3. As shown in FIG. 3, the probe 106 can be attached to a stereotactic device 302. The probe can be attached to the stereotactic device via a mounting device and/or attached directly to the stereotactic device via an attachment mechanism. The probe 106 can be mechanically moved (e.g., by a physician moving the probe) or automatically moved (e.g., moving in response to a signal by a computer) to bring the microcoil 104 and/or the probe into proximity to or in contact with the exposed portion of the central nervous system 102.

The probe 106 can include a fixture that can be configured to conform to an anatomical feature of the central nervous system, decreasing the time required for surgical mapping compared to traditional mapping methods. The contour can include a plurality of microcoils and can conform to the exposed portion of the central nervous system. For example, the fixture can be constructed at least in part of a material that can conform to the exposed portion of the central nervous system and/or the fixture can be constructed of a material in the shape of the exposed portion of the central nervous system. The fixture can include a plurality of microcoils. In an example, the plurality of microcoils can be arranged in a shape or a configuration to facilitate magnetic stimulation of targeted areas of the exposed portion of the central nervous system via magnetic induction. In another example, one or more of the plurality of microcoils can be activated to apply the magnetic stimulation via magnetic induction to certain parts of the exposed portion of the central nervous system.

FIG. 4 illustrates a system 30 that can map the activation in a central nervous system of a subject based on micromagnetic stimulation. The micromagnetic stimulation can be accomplished by the system 10 (the probe 106 coupled to the microcoil 104) as described with respect to FIG. 1. System 30 can also include one or more components, including at least one of an actuator 310 that can receive an indication to send the electric current to one or more microcoils 104, a stimulator 308 that can generate the electric current, a detector 312 that can detect the activation and/or suppression, and a computer 314 that can create and/or update an activation map based on the detected activation and/or suppression.

The actuator 310 can receive an indication to send the electric current to one or more microcoils 104. The actuator 310 can be electrically coupled to the microcoils 104. The electrical coupling can be through a stimulator 308 that can generate the electric current. As an example, the indication received by the actuator 310 can come from a medical professional (e.g., the actuator 310 can be a foot pedal or a handheld device that can receive a mechanical signal from the medical professional). In another example, the actuator 310 can be coupled to the computer 314 and can receive the signal from the computer (e.g., based on a programmed mapping procedure for the specific neurosurgical procedure being performed, an indication of the activation and/or suppression received from the detector 312, and/or a feature uncovered via imaging before or during the neurosurgical procedure).

The actuator 310 can be configured to receive an indication to actuate the stimulator 308 (that can be external to the probe 106 and/or part of the probe) activate one or more of the microcoils 104 to produce a time-varying magnetic field that can induce a current in one or more nerves, thereby activating the one or more nerves within the portion of the central nervous system 102. The actuator can activate one microcoil at a time or can activate a plurality of microcoils at a time.

The detector 312 can be configured to detect the activation or suppression of the portion of the central nervous system and/or the subsequent activation of additional areas of the central nervous system. Information related to the detection by detector 312 can be used to create and/or update a conduction map of the central nervous system. Like the actuator 310, the detector 312 can be part of the probe 106 and/or external to the probe. As an example, the detector can be an optical detector that can detect the activation and/or suppression. The optical detector can use infrared light, ultraviolet light, visible light, and the like, to detect the activation and/or suppression. The detector can also measure the electrical activity of muscles that can detect the activation and/or suppression The detector 312 can be coupled to a computer 314 that can create and/or update the activation map based on the information from the detector 312. In an example, the detector 312 and/or the computer 314 can include a non-transitory memory storing instructions and a processor that executes the instructions to at least receive a signal indicating the activation and/or suppression (e.g., from one or more sensors or imaging devices) and add the activation and/or suppression of the portion of the central nervous system to a conduction map. The detector 312 and/or the computer 314 can also include an output device that can be configured to display a graphical representation of the conduction map and update the graphical representation based on the detected activation and/or suppression of the central nervous system (e.g., the graphical representation can be updated based on a response to activation and/or suppression by each of the one or more microcoils 104).

IV. Methods

Figure 5:
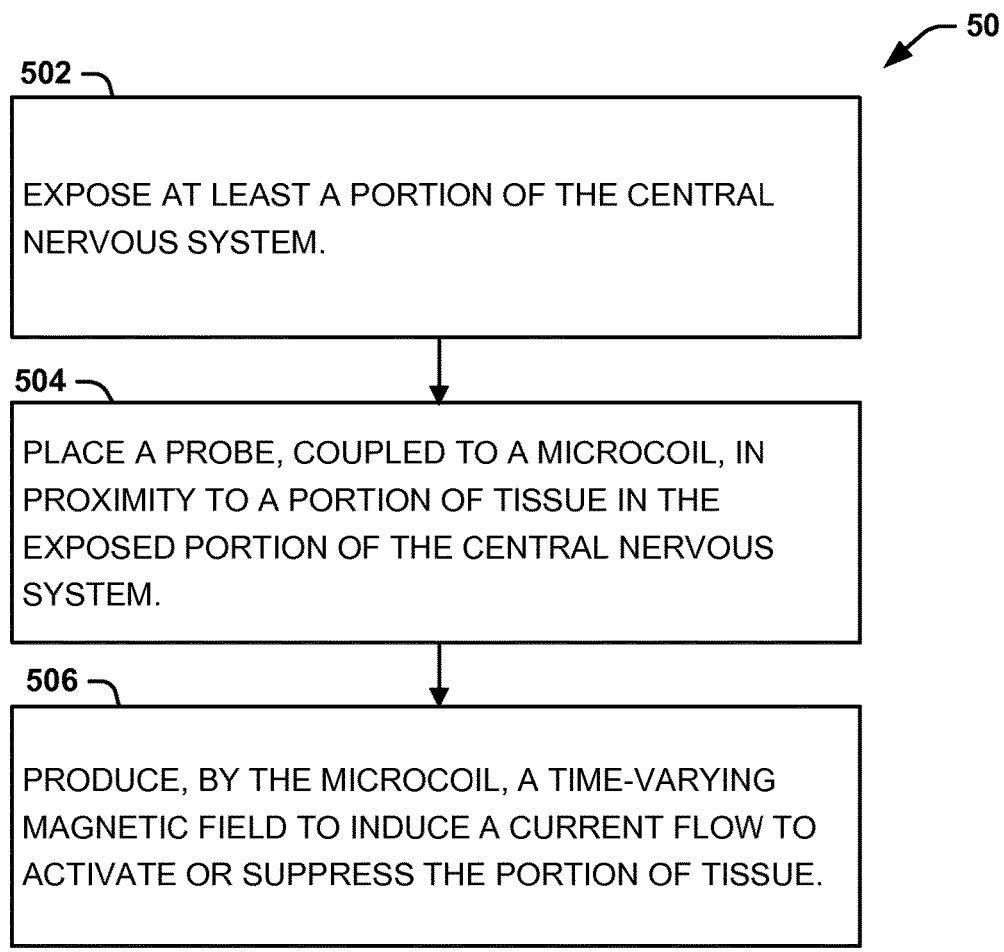
FIG. 5 is a process flow diagram illustrating a method for stimulating one or more areas of the central nervous system of a subject in accordance with another aspect of the present disclosure.

A second aspect of the present disclosure can include methods that can employ micromagnetic stimulation to activate areas of the central nervous system. An example of a method 50 that can stimulate one or more areas of the central nervous system of a subject is shown in FIG. 5. Another example of a method 60 that can map activation in a central nervous system of a subject is shown in FIG. 6.

Figure 6:
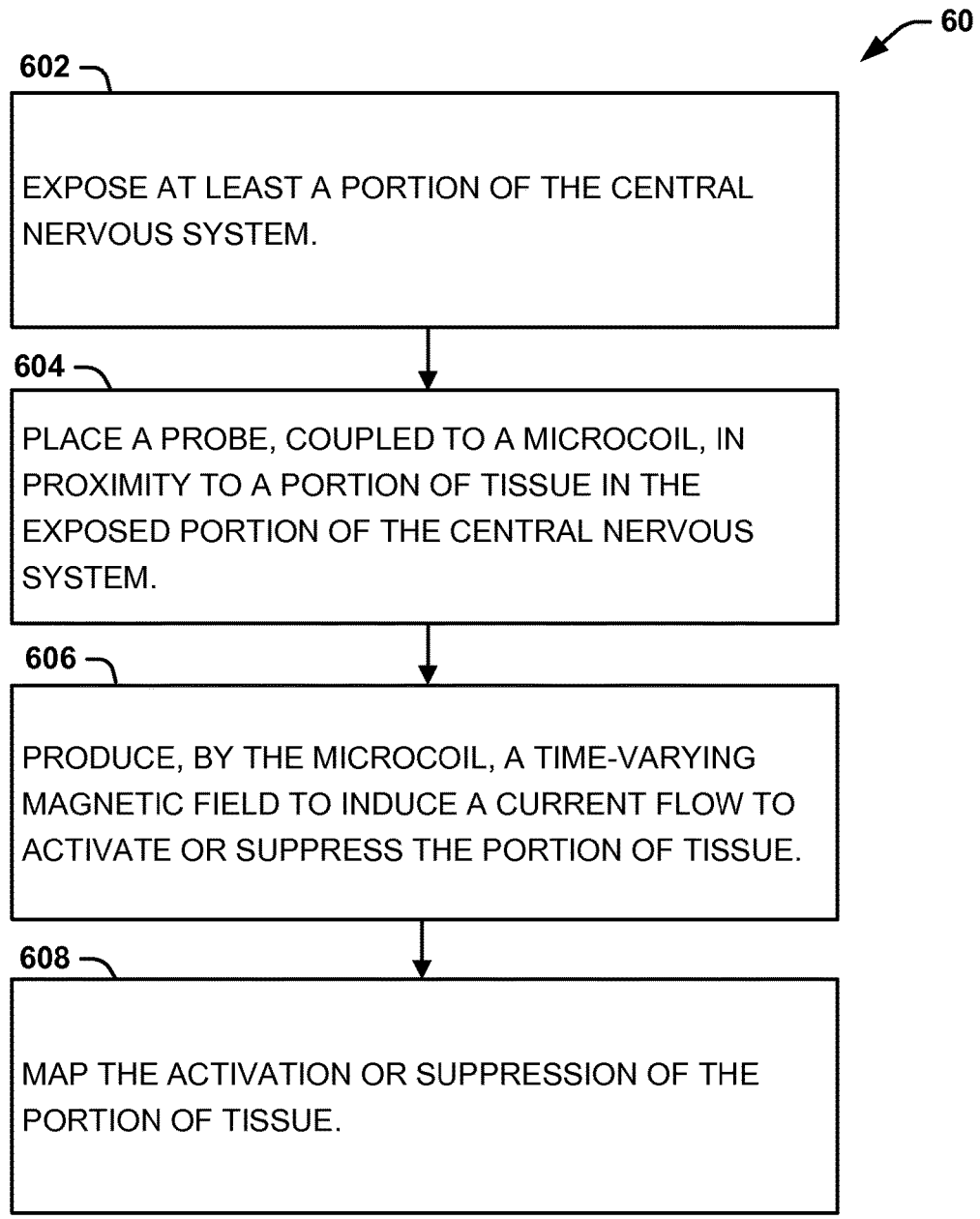
FIG. 6 is a process flow diagram illustrating a method for mapping activation in at least a portion of a central nervous system of a subject in accordance with an aspect of the present disclosure.

The methods 50 of FIG. 5 and 60 of FIG. 6 are illustrated as process flow diagrams with flowchart illustrations. For purposes of simplicity of explanation, the methods 50 of FIGS. 5 and 60 of FIG. 6 are shown and described as executing serially, it is to be understood and appreciated that the present disclosure is not limited by the illustrated order, as some aspects could occur in different orders and/or concurrently with other aspects shown and described herein. Moreover, not all illustrated aspects may be required to implement method 50 or method 60.

In some instances, one or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, some of the steps/acts can be implemented by a system comprising a processor that can access the computer-executable instructions that are stored in a non-transitory memory.

Referring to FIG. 5, an aspect of the present disclosure can include a method 50 for stimulating one or more areas of the central nervous system (CNS) of a subject. The stimulation can be micromagnetic stimulation of the portion of the central nervous system of the subject.

At 502, at least a portion of the subject's central nervous system can be exposed (e.g., during a neurosurgical procedure). At 504, a probe (e.g., probe 106) coupled to one or more microcoils (e.g. a microcoil 104 or a plurality of microcoils) can be placed in proximity to a portion of tissue (e.g., a portion of CNS tissue 102) in the exposed portion of the CNS.

At 506, a time-varying magnetic field can be produced by the microcoil to induce a current flow to activate the portion of tissue. For example, the microcoil can produce the time-varying magnetic field in response to a signal (e.g., generated by stimulator 308). The signal can be generated in response to an indication by a medical professional (e.g., by physically activating actuator 310 and the stimulator 308 can generate the signal in response to an indication from the actuator 310).

Referring now to FIG. 6, an aspect of the present disclosure can include a method 60 for mapping activation in a central nervous system of a subject. Steps 602-606 are similar to steps 502-506 of method 50. For example, at 602, at least a portion of the subject's central nervous system can be exposed (e.g., during a neurosurgical procedure). At 604, a probe (e.g., probe 106) coupled to one or more microcoils (e.g. a microcoil 104 or a plurality of microcoils) can be placed in proximity to a portion of tissue (e.g., CNS tissue 102) in the exposed portion of the CNS. At 606, a time-varying magnetic field can be produced by the microcoil to induce a current flow to activate (or suppress) the portion of tissue.

Based on the activation of the portion of tissue, at 608, the activation of the portion of tissue can be mapped (e.g., an activation map can be created by computer 314, including a non-transitory memory and a processor, in response to the detection of the activation by detector 312). For example, the activation map can include the activated or suppressed portion of tissue and any subsequent areas of conduction that are activated or suppressed due to the activation or suppression of the portion of the tissue. The activated or suppressed portion of tissue can be detected and any subsequent areas that are activated or suppressed (e.g., by a detector 312 coupled to the probe 106), according to an example, and information related to the detected activation or suppression can be sent (e.g., to a computer 314) to be added and/or included in an activation map or suppression map.

V. EXAMPLES

The following example is presented for the purpose of illustration only and is not intended to limit the scope of the appended claims.

Example 1

This example shows that the micromagnetic stimulation (μMS) approach described in connection with the systems and methods above (e.g., using microcoils) can activate brain circuits in a living animal and that submillimeter coils can generate focal electromagnetic fields precisely affecting specific functional pathways without adversely altering the physiology of the animals.

Methods

Animal Subjects

Adult male Syrian golden hamsters were acquired from Charles River Laboratory and housed in the animal vivarium of the Lerner Research Institute on a 12 hr:12 hr light:dark cycle. All procedures performed were approved by the Institutional Animal Care and Use Committee of the Cleveland Clinic, which adheres to the NIH Guide for the Care and Use of Laboratory Animals. A total of 6 animals were used.

Surgical Preparation

Each animal was anesthetized using intramuscular injection of Ketamine/Xyalzine (117/18 mg/kg). Animals were placed on a heating pad inside a sound insulated booth. A rectal thermometer was inserted into the animal and the output of the thermometer relayed to a current regulator of the heating pad to keep the core temperature at 37° C. A tracheostomy was performed using a midline neck incision. A CT-1000 cardiotachometer (CWE, Inc., Ardmore, Pa.) was used to monitor the heart rate and the electrocardiogram (ECG) waveform throughout the surgery and electrophysiological recording period. The animal was then mounted on a head brace, and an occipital and partial parietal craniectomy was performed under a Leica (MZ16F) surgical microscope. Bleeding was controlled using bone wax and gel foam until complete surgical hemostasis was achieved. A micro-aspirator was then used to remove part of the cerebellum overlying the left deep cerebellar nuclei (DCN) and caudal-most part of the right cerebrum to expose the right inferior colliculus (IC). At the completion of surgery, the DCN and IC were exposed and made accessible for electrophysiological recordings.

Supplements of anesthetic were administered every 30-45 min, and the heart rate was kept below 240 beats/min, indicating an adequate depth of anesthesia during the recording session. A camera was mounted on top of a surgical microscope to view the DCN and IC from a dorsal perspective.

Electrophysiological Recordings

Multi-unit extracellular recordings from the IC were performed using electrodes with an impedance of 0.4-0.5 MΩ. The signal from the electrode was amplified 1000× and bandpass filtered (0.3-10 kHz) using a preamplifier (World Precision Instruments; DAM-80). Once conditioned the electrophysiological data was digitized at 40 kHz (NI PCIe-6251, National Instruments, Austin, Tex.) and archived for offline analysis.

Frequency response properties were determined by counting the number of voltage events exceeding −100 mV in response to each of 800 monoaurally presented tonal stimuli (16 intensities and 50 frequencies), each lasting 30 ms (5 ms rise/fall time) and separated by an inter-stimulus interval of 50 ms. The pure tones were delivered through a Beyer Dynamic DT-48 speaker coupled to the left external ear through a conical tube. The voltage events recorded were used to plot frequency response curves from which the characteristic frequency and threshold was calculated for each cluster of neurons. These measurements allowed precise localization of the recording electrode along the frequency axis of the central nucleus of the IC (CNIC).

Magnetic Stimulation Methods

In order to generate a time varying magnetic field in the neuronal tissue, a sub-millimeter size non-ferromagnetic core inductor was used. During the experiments, the microcoil was mounted on a second manipulator and positioned above the dorsal aspect of the DCN and could be controlled remotely from outside the recording chamber. Using the manipulator the coil was positioned approximately 100 μm dorsal to (not touching) the surface of the DCN. Due to variations in the thickness of the coil insulators (~50 μm), the distance above the DCN was variable between the different coils used in the study. In order to establish activation thresholds for each animal, the output voltage of the function generator was increased in 100 mV increments (starting at 100 mV) until a clear IC post-stimulus activation could be observed.

Monophasic rectangular stimulation pulses with different pulse widths and amplitudes were generated by a function generator (AFG3012B, Tektronix Inc. Beaverton, Oreg.) triggered by an analog I/O card (NI PCIe-6251, National Instruments, Austin, Tex.) with an average rate of 2 Hz. The pulses were then amplified by a 1,000-W audio amplifier (PB717X, Pyramid Inc., Brooklyn, N.Y.) and applied to the microcoil for magnetic field generation. The input pulse to the power amplifier and the corresponding output waveform of the power amplifier are shown in FIG. 11f. The outputs of both the power amplifier and the generator were connected to BNC splitters for monitoring with an oscilloscope (DP03012, Tektronix Inc., Beaverton, Oreg.). When referencing "stimulus amplitude," only the input pulse amplitudes to the power amplifier are indicated.

Construction of Coils

A commercial multilayer MEMS RF 0402 inductor (ELJ-RFR10JFB, Panasonic Electronic Devices Corporation of America (PEDCA), Knoxville, Tenn.) with 100 nH inductance, 5.5Ω maximum DC resistance, Q (100 MHz) of 8, self-resonant or maximum frequency of 1.25 GHz, and 400×400×600 μm size (uninsulated dimension) was soldered using a 15-mils 44-resin core solder SN63PB37 (Kester, Itasca, Ill.) on the tip of 34-AWG copper wires with polyimide enamel inner coat and polyurethane over coat (Philmore Mfg., Rockford, Ill.). The two wires were then inserted in a 16¾ G blunt cannula with 150 mm of length. The needle was inserted in a 1 cc syringe and two electrical wires inside were connected to a BNC connector. The BNC was glued with a hot-melt adhesive to the syringe which was then secured to the micromanipulator during the experiments. Finally, the μMS coils were coated with acrylatecopolymer enamel (Revlon, New York, N.Y.) for electrical insulation and water impermeability of the exposed coil terminals.

The μMS coils were thoroughly tested to make sure that the current leak would remain minimal during the magnetic stimulation experiments. This test was important since, if present, such currents could have produced the observed neural stimulation. The test consisted of measuring the insulators impedance by submersing the coils in a physiological solution (0.9% NaCl) together with an electrode. The impedance between each terminal of the pMS coil and the electrode in the solution was measured with a commercial impedance meter (Omega-Tip-Z, World Precision Instruments, Sarasota, Fla.) immediately before and after each experiment. The coils were considered well insulated only when this impedance was greater than 2 MΩ. In addition, the resistance across the microcoil was also tested before and after each experiment using a multimeter (Fluke 115 Digital Multimeter, Everett, Wash.), with normal values ranging from 4.5-4.7Ω.

Analysis of Stimulation Data

A multi-unit analysis method was used to detect the neuronal activities in IC. For this analysis, the stimulus artifact in the IC recording was removed or attenuated using a curve fitting method where the stimulus artifact waveform was considered to be the result of linear LCR circuits. Therefore, the artifact waveform was assumed to be the multiplication of the exponential decay term and sinusoidal term as a result of linear system. In the curve fitting method, the parameters were found minimizing the following cost function L.

$$L = \sum_{t=t_1}^{t_2} (x(t) - x_S(t))^2 + \sum_{t=t_3}^{t_4} (x_S(t))^2, \quad \text{Equation 1}$$

$$x_S(t) = ae^{bt}\sin(ct + d), \quad \text{Equation 2}$$

where $x_S(t)$ is the stimulus artifact, and a, b, c, and d are the parameters to be estimated. In this experiment, $t_1=1$ ms, $t_2=5$ ms, $t_3=10$ ms, and $t_4=30$ ms were selected so that the artifact follows the recorded waveform between $t_1$ and $t_2$ were mainly the stimulus artifact and the artifact decays to zero after $t_3$.

For the curve fitting function, the least squares error method (lsqrcurvefit) was used in MATLAB® (The Mathworks, Inc., Natick, Mass.). After the curve fitting, the artifact was subtracted from the recorded waveform, while the time period from 0-1 ms after the stimulation was set to zero. Once the stimulus artifact was reduced, multi-unit spike units were detected using Offline Sorter (Plexon Inc., Dallas, Tex.).

Statistical Analyses

Statistical analyses were applied to the multi-unit data in order to determine differences between μMS parameters (pulse-width and amplitudes). Statistical significance was accepted with $p<0.001$ using a Kruskal-Wallis test with a Bonferroni correction for multiple comparisons.

Results

Figure 7:
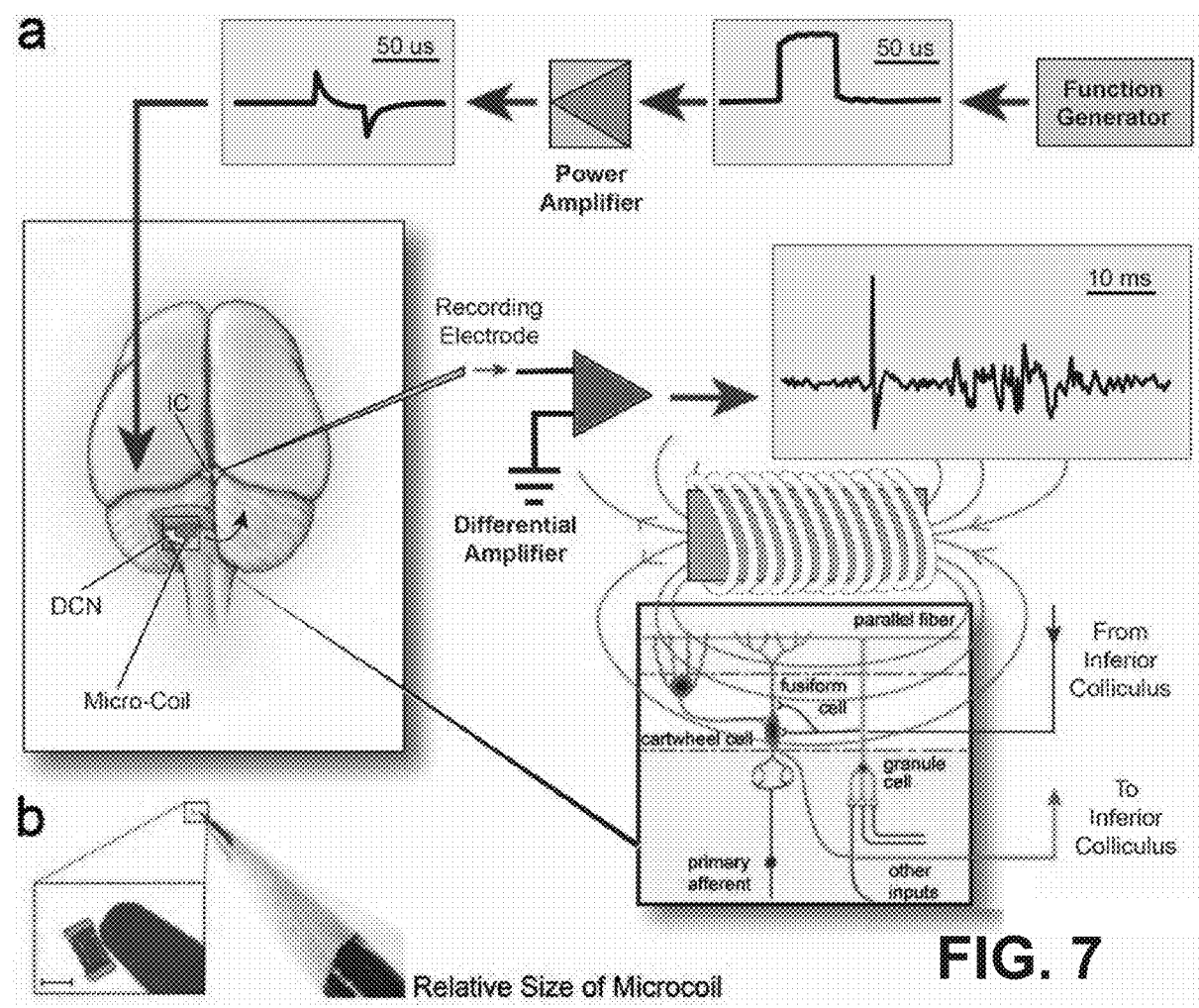
FIG. 7 shows an example illustration of an experimental setup for micromagnetic stimulation.

The trans-synaptic activation of neurons using sub-millimeter size coils was demonstrated by the application of μMS to the dorsal cochlear nucleus (DCN), while measuring the neuronal activity of the contralateral IC in anesthetized hamsters (n=6). Specifically, microcoils were oriented parallel to the media-lateral axis of the DCN while glass pipette recording electrodes were advanced into the contralateral IC, as illustrated in FIG. 7a. Once stable auditory evoked electrophysiological signals were isolated from the IC and the threshold for neuronal activation was determined, a computer-controlled stimulation system randomly presented different amplitudes and pulse-widths of μMS to the DCN. The different parameters of μMS were presented following a 30 second interval in which no stimulation was applied. All electrophysiology data was digitized and analyzed offline.

Figure 8:
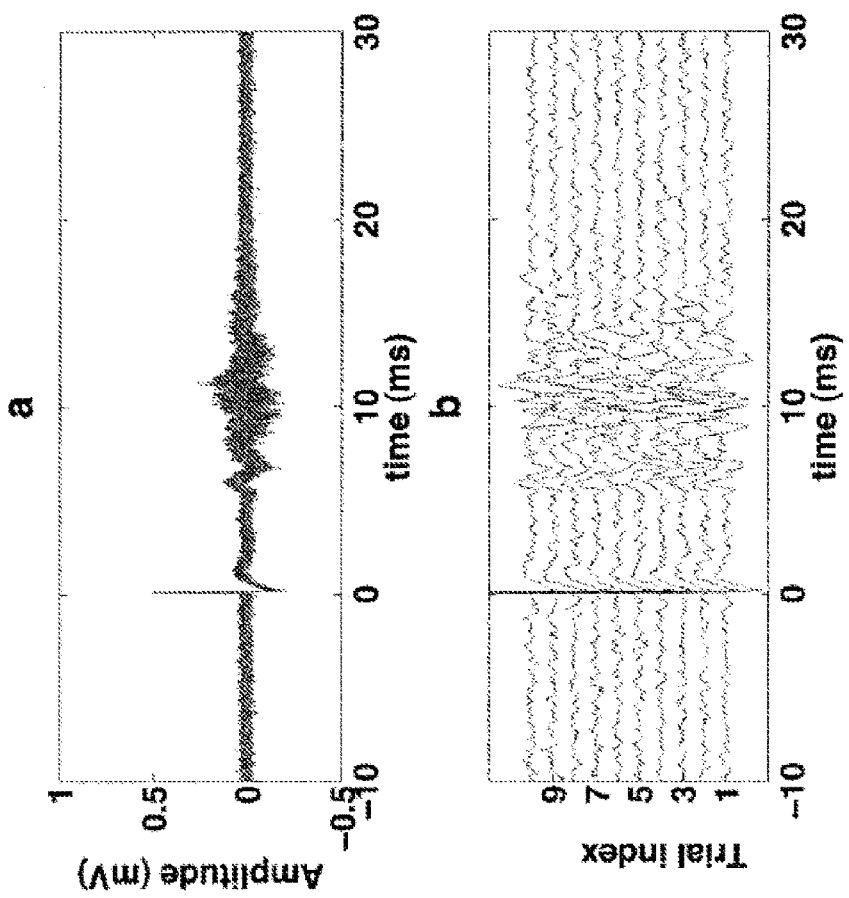
FIG. 8 shows example complex neuronal responses of the inferior colliculus (IC) to micromagnetic stimulation of the deep cerebellar nuclei (DCN)

Activation of the IC with μMS of the DCN

μMS of the DCN was capable of evoking neuronal activation of the IC in all six animals tested in the study. Although variance in the evoked response was observed between experimental animals, likely due to the relative position between the coils and the DCN in each animal, two primary responses were elicited (FIG. 8). The first response consisted of a short latency (~6 ms) synchronized neuronal activation, observed in 67% (4/6) of the animals tested. The second response consisted of a longer latency (mean latency ~15 ms), less synchronized response, observed in 100% of the animals tested. The short latency synchronized activation had little temporal variation and high reproducibility in response to each μMS pulse. In contrast, the long latency evoked response was rather asynchronous and more distributed in duration, suggestive of poly-synaptic orthodromic activation.

Effects of μMS Amplitude and Pulse-Width on IC Activation

Figure 9:
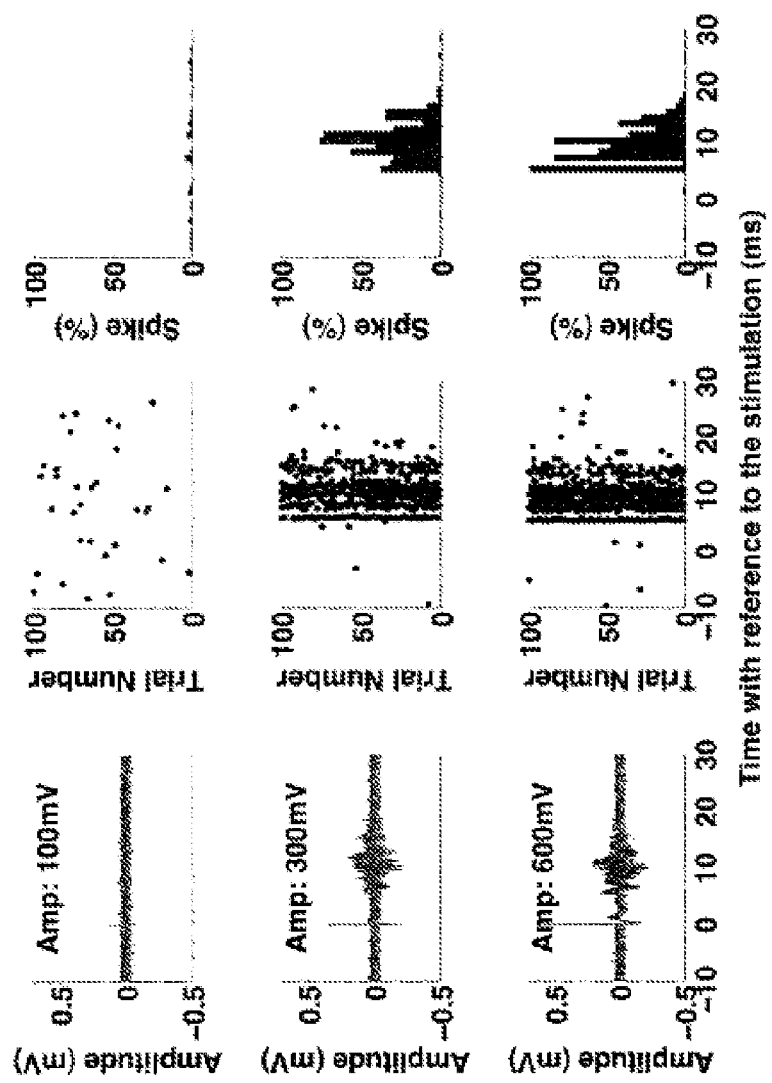
FIG. 9 shows a differential neuronal response of IC to different amplitudes of micromagnetic stimulation of the DCN.

In order to characterize the parameters of μMS, the effects of different amplitudes and pulse-width of stimulation on IC activity were examined. FIG. 9 illustrates the effects of three different stimulus amplitudes on neuronal activity in the IC. As shown, the lowest level of stimulation did not evoke a response in the IC. With an increase in stimulus amplitude, the short latency neuronal response became synchronized and deterministic, with 100% firing probability for the highest amplitude of stimulation.

Figure 10:
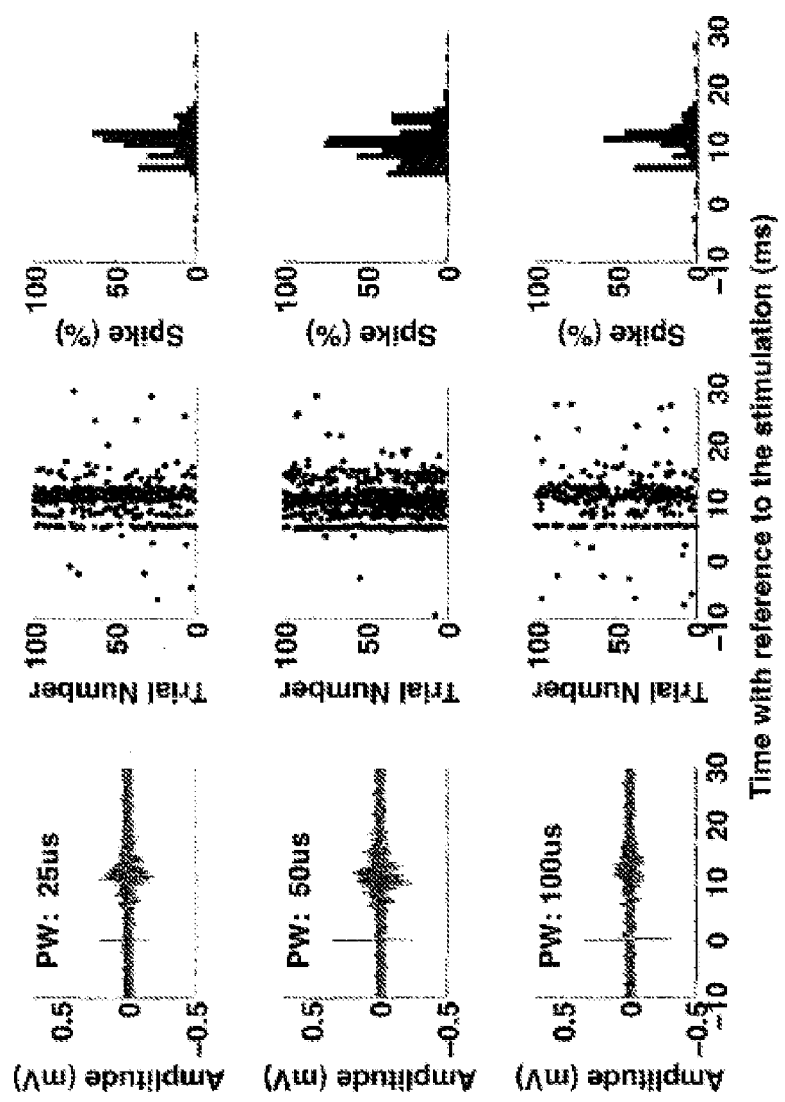
FIG. 10 shows a differential neuronal response of the IC to different pulse widths of micromagnetic stimulation of the DCN.

FIG. 10 shows an example of the IC evoked response for three different stimulus pulse-widths (25, 50, and 100 μs) for a single amplitude of stimulation in the same animal. As shown, all three pulse-widths at this amplitude resulted in activation of the IC. Interestingly, the middle pulse-width (50 μs) resulted in the greatest activation of the IC. Specifically, the average number of evoked spikes between 5 ms and 20 ms after stimulation with pulse-widths of 25, 50 and 100 μs were 3.1±1.2, 4.8±1.2, and 2.5±1.2 (mean±s.d.), respectively. Statistical analysis demonstrated that the 50 μs stimulation significantly evoked more spikes compared to 25 or 100 μs ($p<0.001$; Kruskal-Wallis test with Bonferroni correction).

Summary of Responses to μMS

Figure 11:
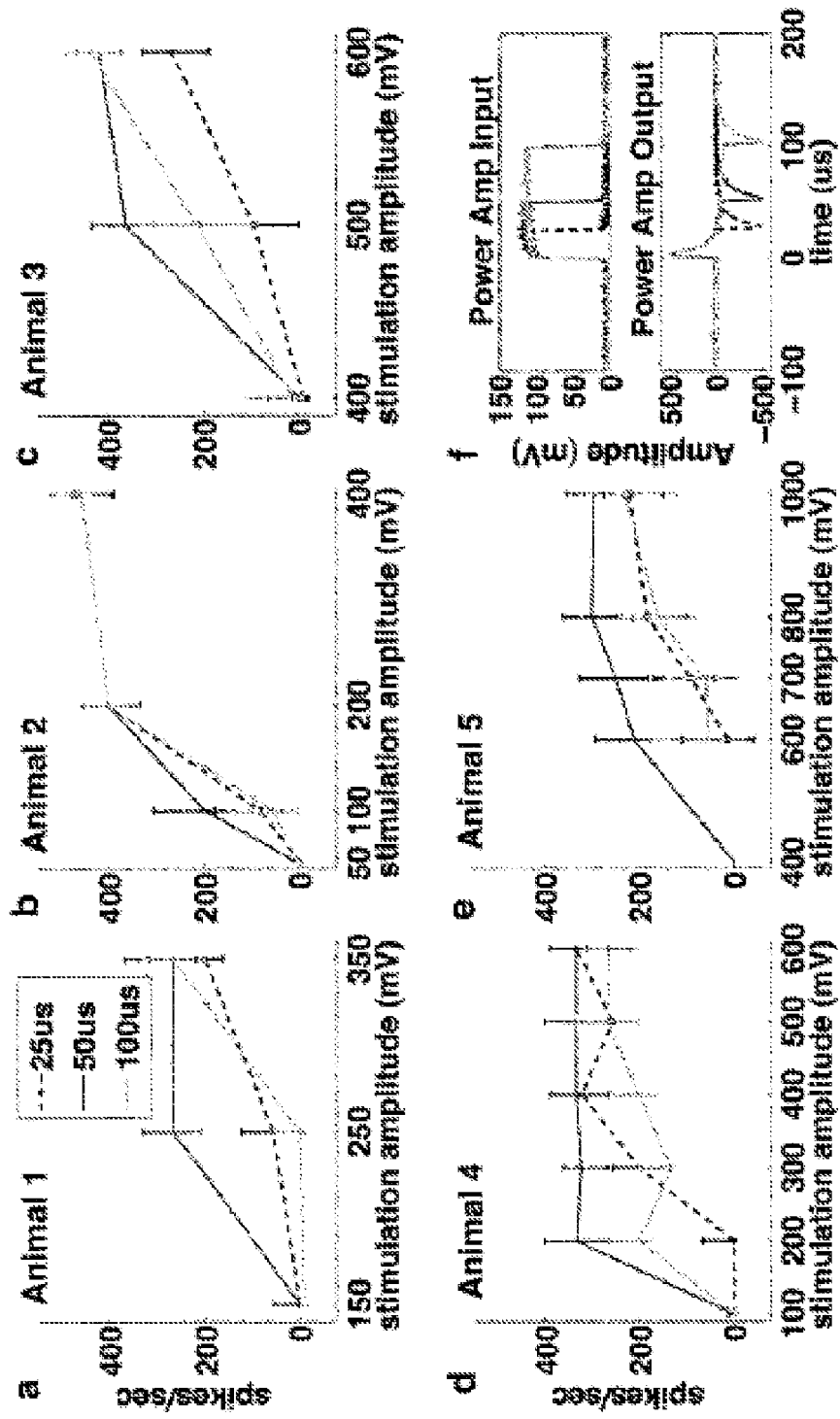
FIG. 11 shows a summary of affects of micromagnetic stimulation amplitude and pulse-width modulation on IC activities.

In order to further evaluate the relationship between the amplitude and pulse-width of μMS, the IC evoked potentials for all stimulation parameters tested were examined (FIG. 11). One animal was excluded from this comparison because only a single pulse-width was tested. To compare across animals, the multi-unit spike rates were normalized after each stimulus pulse (5 to 20 ms post stimulus onset) for each of the different parameters of stimulation. The normalization was performed by subtracting the mean baseline firing rate during the period before stimulation (−100 to −5 ms) from that during the post stimulation period. The pulse-widths were fixed at 25 μs, 50 μs and 100 μs, while the amplitudes of stimulation were different for each animal, as the threshold for activation of the IC was variable between animals. Each stimulation parameter analyzed consisted of 100 stimulation pulses with an average of 500 ms between two consecutive μMS pulses. As illustrated (FIG. 11), the neuronal firing rate increased for all animals as the stimulation amplitude increased, regardless of pulse-width. Regarding the effects of pulse-width, in the moderate range of stimulus amplitudes (i.e. above threshold but not saturated), the 50 μs pulsewidth generated a stronger evoked response than either 25 μs or 100 μs pulsewidth ($p<0.001$ for each animal; Kruskal-Wallis test with a Bonferroni correction).

Controls: Recording from Non-Related Cortex and Following CN Ablation

To demonstrate that the μMS evoked responses were biological in nature and that the spatial specificity of stimulation was restricted to the auditory pathway, two control experiments were performed. In the first experiment, the stimulus-evoked response was recorded from the IC before and after the animal was given a lethal overdose of anesthetic. Before the overdose was administered, a μMS stimulus that evoked a clear and robust IC response was presented. After overdose of anesthetic, the evoked response was completed abolished indicating that the evoked response was biological in nature. In a second control, it was shown that the applied magnetic field had spatial specificity to the auditory pathway. In order to demonstrate this, μMS evoked neuronal recordings were performed in other parts of the brain functionally irrelevant to CN-IC auditory pathway, but within close proximity to the IC. In addition, recordings were collected from the IC after the CN had been surgically ablated. As a further control, the auditory evoked response in each recording area was examined to demonstrate that it was present when recording from the IC and that it was absent when recording from the visual pathway and after the CN had been ablated.

Figure 12:
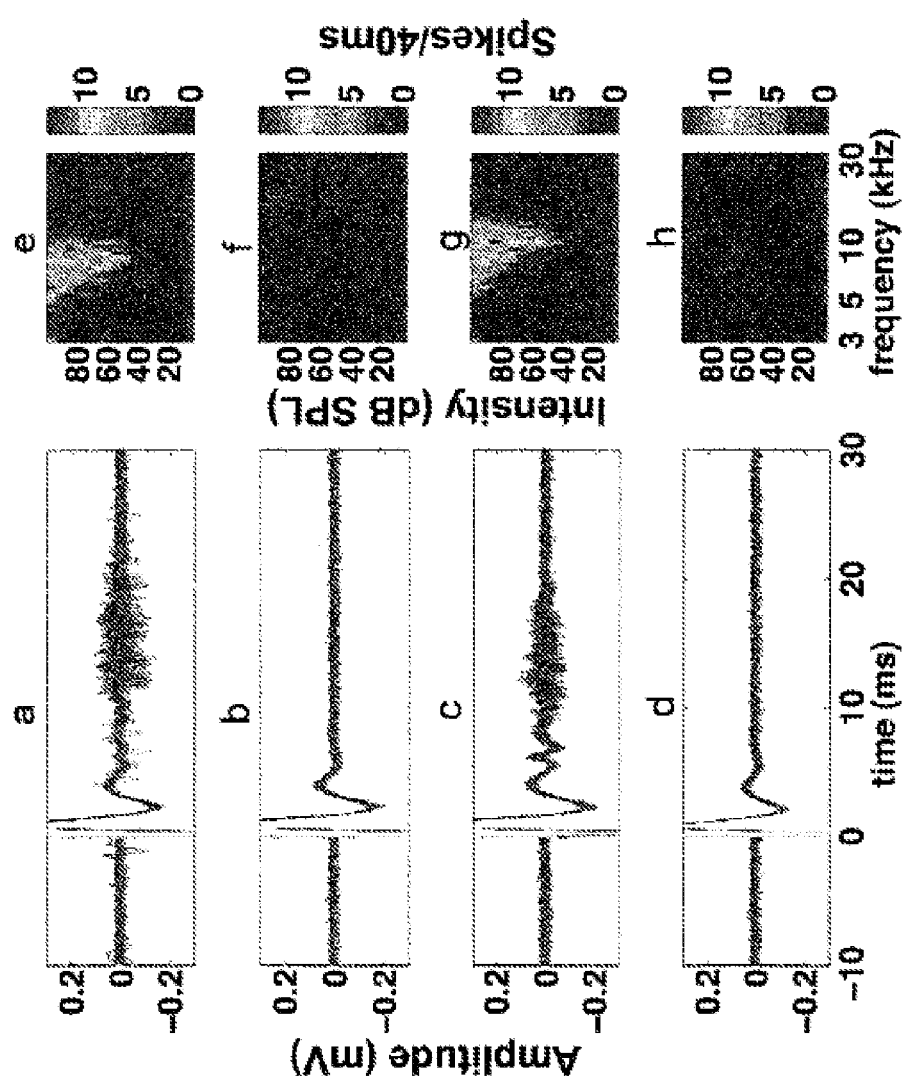
FIG. 12 shows example neuronal responses to micromagnetic stimulation of the DCN in the IC.

FIG. 12 illustrates the results of the other control experiments. FIGS. 12a and 12e show the μMS and auditory evoked activity of the first IC recording site, respectively. As seen, the application of μMS to the DCN and auditory stimuli resulted in robust neuronal responses in the IC. When the recording electrode was placed in the visual cortex, where there is no known direct connection from IC or CN, no μMS or auditory evoked response could be elicited (FIGS. 12b, 12f). When the recording electrode was placed back in IC, the μMS and auditory evoked response was obtained (FIGS. 12c, 12g), which demonstrates that the CN-IC pathway was still intact. Finally, after the CN had been ablated, the μMS and auditory evoked responses were abolished (FIGS. 12d, 12h). The disappearance of the neuronal activities in IC evoked by sound stimulation indicates proper removal of CN and further supports that the previous μMS evoked responses were elicited via the auditory pathway. Moreover, since the stimulus artifact waveforms were similar for all recordings, the activation of IC neurons was not by direct stimulation of IC, but rather via activation of pathways projecting to the IC.

From the above description, those skilled in the art will perceive improvements, changes and modifications. Such improvements, changes and modifications are within the skill of one in the art and are intended to be covered by the appended claims.

What is claimed is:
1. A system comprising:
a probe comprising:
a fixture configured to conform to an exposed portion of a patient's central nervous system without penetrating the exposed portion of the patient's central nervous system; and a plurality of microcoils arranged on the fixture, each having a geometric shape to focus a magnetic field to a depth within the exposed portion of the patient's central nervous system to activate conduction in one or more neurons at the depth within the exposed portion of the patient's central nervous system, wherein the plurality of microcoils are configured to generate a time-varying magnetic field to activate conduction in the one or more neurons at the depth within the exposed portion of the patient's central nervous system via electromagnetic induction in response to an applied current, and a mounting apparatus to attach the probe to a stereotactic device attached to the patient.

2. The system of claim 1, wherein the time-varying magnetic field induces current flow to activate conduction in the one or more neurons.

3. The system of claim 1, wherein the probe is coupled to an actuator configured to send an electric current to at least one of the plurality of microcoils to apply the electromagnetic induction upon receipt of a signal.

4. The system of claim 1, wherein the probe is coupled to a detector configured to detect the activation of conduction in the one or more neurons within the exposed portion of the central nervous system, wherein the detector sends a signal to update a conduction map based on the detected activation of conduction in the one or more neurons within the exposed portion of the central nervous system.

5. The system of claim 4, wherein the detector is coupled to a computing device comprising:

a non-transitory memory storing instructions;

a processor that executes the instructions to at least:

receive the signal from the detector indicating the detected activation of conduction in the one or more neurons within the exposed portion of the central nervous system; and update the conduction map based on the detected activation of conduction in the one or more neurons within the exposed portion of the central nervous system; and an output device configured to display a graphical representation of the conduction map and update the graphical representation based on the detected activation of conduction in the one or more neurons within the exposed portion of the central nervous system.

6. A method comprising:

exposing a portion of a patient's central nervous system;

attaching a probe to a stereotactic device attached to the patient;

placing the probe, attached to the stereotactic device, in contact with the exposed portion of the patient's central nervous system without penetrating the exposed portion of the patient's central nervous system, wherein the probe comprises:

a fixture configured to conform to an anatomical feature of the exposed portion of the patient's central nervous system; and a plurality of microcoils arranged on the fixture, each of the plurality of microcoils having a geometric shape to focus a magnetic field to a depth within the exposed portion of the patient's central nervous system, wherein the placement of the probe is guided by the stereotactic device;

producing, by at least one of the plurality of microcoils of the probe attached to the stereotactic device, a time-varying magnetic field focused to the depth to induce a current flow to activate conduction within one or more neurons at the depth within the exposed portion of the patient's central nervous system; and moving the probe attached to the stereotactic device.

7. The method of claim 6, further comprising detecting, by an infrared detector coupled to the probe, the activation of the conduction within the one or more neurons.

8. The method of claim 7, further comprising transmitting data related to the detected activation to a system comprising a processor for addition to an activation map of the central nervous system.

9. The method of claim 6, wherein the at least one of the plurality of microcoils produces the magnetic field upon receiving a signal from an actuator controlled by a medical professional.

10. The method of claim 6, wherein each of the plurality of microcoils is configured to stimulate a corresponding portion of the one or more neurons.

11. The method of claim 10, wherein each of the plurality of microcoils is configured to stimulate a respective portion of the one or more neurons upon activation by an actuator device controlled by a medical professional.

* * * * *